US006802713B1

(12) United States Patent
Chishti et al.

(10) Patent No.: US 6,802,713 B1
(45) Date of Patent: Oct. 12, 2004

(54) DEFINING TOOTH-MOVING APPLIANCES COMPUTATIONALLY

(75) Inventors: Muhammad Chishti, Sunnyvale, CA (US); Elena I. Pavlovskaia, San Francisco, CA (US); Gregory P. Bala, San Jose, CA (US); Brian Freyburger, San Francisco, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

(21) Appl. No.: 10/691,755

(22) Filed: Oct. 22, 2003

Related U.S. Application Data

(63) Continuation of application No. 10/228,885, filed on Aug. 26, 2002, now Pat. No. 6,682,346, which is a continuation of application No. 09/169,034, filed on Oct. 8, 1998, now Pat. No. 6,471,511.

(51) Int. Cl.[7] .................................................. A61C 3/00
(52) U.S. Cl. ............................................. 433/24; 433/6
(58) Field of Search ............................... 433/6, 24, 213

(56) References Cited

U.S. PATENT DOCUMENTS

| 3,660,900 A | 5/1972 | Andrews |
| 3,860,803 A | 1/1975 | Levine |
| 4,348,178 A | 9/1982 | Kurz |

(List continued on next page.)

FOREIGN PATENT DOCUMENTS

| FR | 2 369 828 | 6/1978 |
| WO | WO 98/32394 | 7/1988 |
| WO | WO 94/10935 | 5/1994 |

OTHER PUBLICATIONS

Biostar Operation & Training Manual, Great Lakes Orthodontics, Ltd. 199 Fire Tower Drive, Tonawanda, New York, 14150–5890, 20 pages total.

Chiappone, (1980). "Constructing the gnathologic setup and positioner" J. Clin. Orthod. 14:121–133.

Cottingham, (1969). "Gnathologic clear plastic positioner" Am. J. Orthod. 55:23–31.

(List continued on next page.)

*Primary Examiner*—John J. Wilson
(74) *Attorney, Agent, or Firm*—Townsend and Townsend and Crew LLP; Bao Tran, Esq.

(57) ABSTRACT

Methods and corresponding apparatus for segmenting an orthodontic treatment path into clinically appropriate substeps for repositioning the teeth of a patient include providing a digital finite element model of the shape and material of each of a sequence of appliances to be applied to a patient; providing a digital finite element model of the teeth and related mouth tissue of the patient; computing the actual effect of the appliances on the teeth by analyzing the finite elements models computationally; and evaluating the effect against clinical constraints. The appliances can be braces, polymeric shells, or other forms of orthodontic appliance.

15 Claims, 7 Drawing Sheets

U.S. PATENT DOCUMENTS

| | | | |
|---|---|---|---|
| 4,504,225 | A | 3/1985 | Yoshii |
| 4,505,673 | A | 3/1985 | Yoshii |
| 4,755,139 | A | 7/1988 | Abatte et al. |
| 4,793,803 | A | 12/1988 | Martz |
| 4,798,534 | A | 1/1989 | Breads |
| 4,836,778 | A | 6/1989 | Baumrind et al. |
| 4,856,991 | A | 8/1989 | Breads et al. |
| 4,936,862 | A | 6/1990 | Walker et al. |
| 5,011,405 | A | 4/1991 | Lemchen |
| 5,017,133 | A | 5/1991 | Miura |
| 5,035,613 | A | 7/1991 | Breads et al. |
| 5,055,039 | A | 10/1991 | Abbatte et al. |
| 5,059,118 | A | 10/1991 | Breads et al. |
| 5,139,419 | A | 8/1992 | Andreiko et al. |
| 5,186,623 | A | 2/1993 | Breads et al. |
| 5,273,429 | A | 12/1993 | Rekow et al. |
| 5,338,198 | A | 8/1994 | Wu et al. |
| 5,340,309 | A | 8/1994 | Robertson |
| 5,342,202 | A | 8/1994 | Deshayes |
| 5,368,478 | A | 11/1994 | Andreiko |
| 5,382,164 | A | 1/1995 | Stern |
| 5,395,238 | A | 3/1995 | Andreiko et al. |
| 5,431,562 | A | 7/1995 | Andreiko et al. |
| 5,447,432 | A | 9/1995 | Andreiko et al. |
| 5,452,219 | A | 9/1995 | Dehoff et al. |
| 5,454,717 | A | 10/1995 | Andreiko et al. |
| 5,456,600 | A | 10/1995 | Andreiko et al. |
| 5,474,448 | A | 12/1995 | Andreiko et al. |
| 5,533,895 | A | 7/1996 | Andreiko et al. |
| 5,542,842 | A | 8/1996 | Andreiko et al. |
| 5,549,476 | A | 8/1996 | Stern |
| 5,587,912 | A | 12/1996 | Andersson et al. |
| 5,605,459 | A | 2/1997 | Kuroda et al. |
| 5,607,305 | A | 3/1997 | Andersson et al. |
| 5,621,648 | A | 4/1997 | Crump |
| 5,645,421 | A | 7/1997 | Slootsky |
| 5,683,243 | A | 11/1997 | Andreiko et al. |
| 5,848,115 | A | 12/1998 | Little et al. |
| 6,217,334 | B1 | 4/2001 | Hultgren |

OTHER PUBLICATIONS

Curelton, (1996). "Correcting malaligned mandibular incisors with removable retainers" J. Clin. Orthod. 30:390–395.

Doyle, (2000). "Digital Dentistry" Computer Graphics World, Oct. 2000 pp. 50–52, 54.

Elsasser, (1950). "Some observations on the history and uses of the Kesling positioner" Am. J. Orthod. 36:368–374.

Kamada et al., (1984). "Case reports on tooth positioners using LTV vinyl silicone rubber" J. Nihon University School of Dentistry 26(1):11–29.

Kamada et al., (1982). "Construction of tooth positioners with LTV vinyl silicone rubber and some case reports" J. Nihon University School of Dentistry 24(1):1–27.

Kesling, (1946). "Coordinating the predetermined pattern and tooth positioning with conventional treatment" Am. J. Orthod. Oral. Surg. 32:285–293.

Kesling, (1945). "The philosophy of the tooth positioner appliance" Am. J. Orthod. Oral. Surg. 31(6):297–304.

Kleemann et al., (1996). "The speed positioner" J. Clin. Orthod. 30:673–680.

Kuroda et al., (1996). "Three–dimensional dental cast analyzing system using laser scanning" Am. J. Orthod. Dentofac. Orthop. 110:365–369.

Nippon Dental review "New orthodontic device–dynamic positioner (.D.P.)–I. Approach to the proposal of D.P. and transparent silicone rubber" (1980) 452:61–74.

Nippon Dental Review "New orthodontic device–dynamic positioner (D.P.)–II. Pratical application and construction of D.P." (1980) 454:107–130.

Nippon Dental Review "New orthodontic device–dynamic positioner (D.P.)–III. Case reports of reversed occlusion" (1980) 457:146–164.

Nippon Dental Review "New orthodontic device–dynamic positioner (D.P.)–Case reports of reversed occlusion" (1980) 458:112–129.

Nishiyama et al., (1977). "A new construction of tooth repositioner by LTV vinyl silicone rubber" J. Nihon University School of Dentistry 19(2):93–102.

Raintree Essix.TM. & ARS Materials, Inc., Raintree Essix.TM., Technical Magazine Table of Contents and Essix.TM. Applications, http://www.essix.com/magazine/default.html (Aug. 13, 1997) 7 pages total.

Redmond et al. (2000). "Clinical Implications of Digital Orthodontics," Am. J. Orthodont. Dentofacial Orthopedics 117(2):240–242.

Shilliday, (1971). "Minimizing finishing problems with the mini–positioner" Am. J. Orthod. 59:596–599.

Warunek et al., (1989). "Clinical use of silicone elastomer appliances" JCO XXIII(10):694–700.

Warunek et al., (1989). "Physical and mechanical properties of elastomers in orthodontic positioners" Am. J. Orthod. Dentofac. Orthop. 95:388–400.

Wells. (1970). "Application of the positioner appliance in orthodontic treatment" Am. J. Orthodont. 58:351–366.

DEFINING TOOTH-MOVING APPLIANCES COMPUTATIONALLY

CROSS-REFERENCES TO RELATED APPLICATIONS

The present application is a continuation of U.S. application Ser. No. 10/228,885, filed Aug. 26, 2002, now U.S. Pat. No. 6,682,346, which was a continuation of U.S. application Ser. No. 09/169,034, filed Oct. 8, 1998, now U.S. Pat. No. 6,471,511.

This application is related to commonly-owned U.S. application Ser. No. 09/686,190, filed Oct. 10, 2000, and U.S. application Ser. No. 09/169,036, filed Oct. 8, 1998, now U.S. Pat. No. 6,450,807, the full disclosures of which are incorporated herein by reference.

BACKGROUND OF THE INVENTION

The present invention relates to computational orthodontics.

In orthodontic treatment, a patient's teeth are moved from an initial to a final position using any of a variety of appliances. An appliance exerts force on the teeth by which one or more of them are moved or held in place, as appropriate to the stage of treatment.

BRIEF SUMMARY OF THE INVENTION

The present invention provides methods and apparatus for defining appliance configurations at the steps of a process of repositioning teeth from an initial tooth arrangement to a final tooth arrangement. The invention can operate to define how repositioning is accomplished by a series of appliances or by a series of adjustments to appliances configured to reposition individual teeth incrementally. The invention can be applied advantageously to specify a series of appliances formed as polymeric shells having the tooth-receiving cavities, that is, shells of the kind described in the above-mentioned U.S. application Ser. No. 09/169,276, filed Oct. 8, 1998 now abandoned.

A patient's teeth are repositioned from an initial tooth arrangement to a final tooth arrangement by making a series of incremental position adjustments using appliances specified in accordance with the invention. In one implementation, the invention is used to specify shapes for the above-mentioned polymeric shell appliances. The first appliance of a series will have a geometry selected to reposition the teeth from the initial tooth arrangement to a first intermediate arrangement. The appliance is intended to be worn until the first intermediate arrangement is approached or achieved, and then one or more additional (intermediate) appliances are successively placed on the teeth. The final appliance has a geometry selected to progressively reposition teeth from the last intermediate arrangement to a desired final tooth arrangement.

The invention specifies the appliances so that they apply an acceptable level of force, cause discomfort only within acceptable bounds, and achieve the desired increment of tooth repositioning in an acceptable period of time. The invention can be implemented to interact with other parts of a computational orthodontic system, and in particular to interact with a path definition module that calculates the paths taken by teeth as they are repositioned during treatment.

In general, in one aspect, the invention provides methods and corresponding apparatus for segmenting an orthodontic treatment path into clinically appropriate substeps for repositioning the teeth of a patient. The methods include providing a digital finite element model of the shape and material of each of a sequence of appliances to be applied to a patient; providing a digital finite element model of the teeth and related mouth tissue of the patient; computing the actual effect of the appliances on the teeth by analyzing the finite elements models computationally; and evaluating the effect against clinical constraints. Advantageous implementations can include one or more of the following features. The appliances can be braces, including brackets and archwires, polymeric shells, including shells manufactured by stereo lithography, retainers, or other forms of orthodontic appliance. Implementations can include comparing the actual effect of the appliances with an intended effect of the appliances; and identifying an appliance as an unsatisfactory appliance if the actual effect of the appliance is more than a threshold different from the intended effect of the appliance and modifying a model of the unsatisfactory appliance according to the results of the comparison. The model and resulting appliance can be modified by modifying the shape of the unsatisfactory appliance, by adding a dimple, by adding material to cause an overcorrection of tooth position, by adding a ridge of material to increase stiffness, by adding a rim of material along a gumline to increase stiffness, by removing material to reduce stiffness, or by redefining the shape to be a shape defined by the complement of the difference between the intended effect and the actual effect of the unsatisfactory appliance. The clinical constraints can include a maximum rate of displacement of a tooth, a maximum force on a tooth, and a desired end position of a tooth. The maximum force can be a linear force or a torsional force. The maximum rate of displacement can be a linear or a angular rate of displacement. The apparatus of the invention can be implemented as a system, or it can be implemented as a computer program product, tangibly stored on a computer-readable medium, having instructions operable to cause a computer to perform the steps of the method of the invention.

Among the advantages of the invention are one or more of the following. Appliances specified in accordance with the invention apply no more than orthodontically acceptable levels of force, cause no more than an acceptable amount of patient discomfort, and achieve the desired increment of tooth repositioning in an acceptable period of time. The invention can be used to augment a computational or manual process for defining tooth paths in orthodontic treatment by confirming that proposed paths can be achieved by the appliance under consideration and within user-selectable constraints of good orthodontic practice. Use of the invention to design aligners allows the designer (human or automated) to finely tune the performance of the aligners with respect to particular constraints. Also, more precise orthodontic control over the effect of the aligners can be achieved and their behavior can be better predicted than would otherwise be the case. In addition, computationally defining the aligner geometry facilitates direct aligner manufacturing under numerical control.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

Like reference numbers and designations in the various drawings indicate like elements.

DETAILED DESCRIPTION OF THE INVENTION

In the present invention, systems and methods are provided for defining appliance configurations or changes to appliance configurations for incrementally moving teeth. The tooth movements will be those normally associated with orthodontic treatment, including translation in all three orthogonal directions relative to a vertical centerline, rotation of the tooth centerline in the two orthodontic directions ("root angulation" and "torque"), as well as rotation about the centerline.

Figure 1:
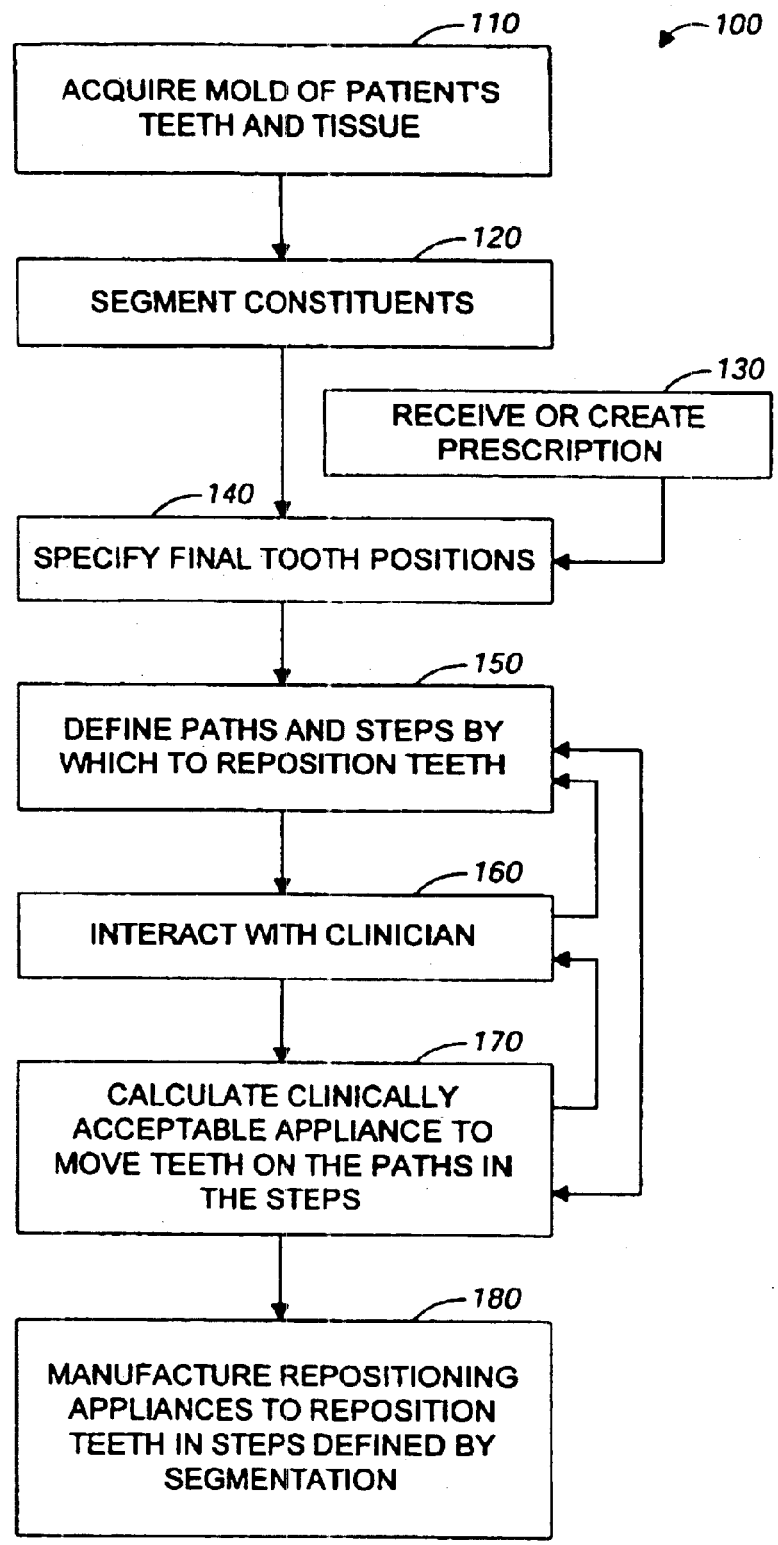
FIG. 1 is a flowchart of a process of specifying a course of treatment including a subprocess for calculating aligner shapes in accordance with the invention.

FIG. 1 illustrates the general flow of an exemplary process 100 for defining and generating repositioning appliances for orthodontic treatment of a patient. The process 100 includes the methods, and is suitable for the apparatus, of the present invention, as will be described. The computational steps of the process are advantageously implemented as computer program modules for execution on one or more conventional digital computers.

As an initial step, a mold or a scan of patient's teeth or mouth tissue is acquired (110). This step generally involves taking casts of the patient's teeth and gums, and may also involve taking wax bites, direct contact scanning, x-ray imaging, tomographic imaging, sonographic imaging, and other techniques for obtaining information about the position and structure of the teeth, jaws, gums and other orthodontically relevant tissue. From the data so obtained, a digital data set is derived that represents the initial (that is, pretreatment) arrangement of the patient's teeth and other tissues.

The initial digital data set, which may include both raw data from scanning operations and data representing surface models derived from the raw data, is processed to segment the tissue constituents from each other (step 120). In particular, in this step, data structures that digitally represent individual tooth crowns are produced. Advantageously, digital models of entire teeth are produced, including measured or extrapolated hidden surfaces and root structures.

The desired final position of the teeth—that is, the desired and intended end result of orthodontic treatment—can be received from a clinician in the form of a prescription, can be calculated from basic orthodontic principles, or can be extrapolated computationally from a clinical prescription (step 130). With a specification of the desired final positions of the teeth and a digital representation of the teeth themselves, the final position and surface geometry of each tooth can be specified (step 140) to form a complete model of the teeth at the desired end of treatment. Generally, in this step, the position of every tooth is specified. The result of this step is a set of digital data structures that represents an orthodontically correct repositioning of the modeled teeth relative to presumed-stable tissue. The teeth and tissue are both represented as digital data.

Having both a beginning position and a final position for each tooth, the process next defines a tooth path for the motion of each tooth. The tooth paths are optimized in the aggregate so that the teeth are moved in the quickest fashion with the least amount of round-tripping to bring the teeth from their initial positions to their desired final positions. (Round-tripping is any motion of a tooth in any direction other than directly toward the desired final position. Round-tripping is sometimes necessary to allow teeth to move past each other.) The tooth paths are segmented. The segments are calculated so that each tooth's motion within a segment stays within threshold limits of linear and rotational translation. In this way, the end points of each path segment can constitute a clinically viable repositioning, and the aggregate of segment end points constitute a clinically viable sequence of tooth positions, so that moving from one point to the next in the sequence does not result in a collision of teeth.

The threshold limits of linear and rotational translation are initialized, in one implementation, with default values based on the nature of the appliance to be used. More individually tailored limit values can be calculated using patient-specific data. The limit values can also be updated based on the result of an appliance-calculation (step 170, described later), which may determine that at one or more points along one or more tooth paths, the forces that can be generated by the appliance on the then-existing configuration of teeth and tissue is incapable of effecting the repositioning that is represented by one or more tooth path segments. With this information, the subprocess defining segmented paths (step 150) can recalculate the paths or the affected subpaths.

At various stages of the process, and in particular after the segmented paths have been defined, the process can, and generally will, interact with a clinician responsible for the treatment of the patient (step 160). Clinician interaction can be implemented using a client process programmed to receive tooth positions and models, as well as path information from a server computer or process in which other steps of process 100 are implemented. The client process is advantageously programmed to allow the clinician to display an animation of the positions and paths and to allow the clinician to reset the final positions of one or more of the teeth and to specify constraints to be applied to the segmented paths. If the clinician makes any such changes, the subprocess of defining segmented paths (step 150) is performed again.

The segmented tooth paths and associated tooth position data are used to calculate clinically acceptable appliance configurations (or successive changes in appliance configuration) that will move the teeth on the defined treatment path in the steps specified by the path segments (step 170). Each appliance configuration represents a step along the treatment path for the patient. The steps are defined and calculated so that each discrete position can follow by straight-line tooth movement or simple rotation from the tooth positions achieved by the preceding discrete step and so that the amount of repositioning required at each step involves an orthodontically optimal amount of force on the patient's dentition. As with the path definition step, this appliance calculation step can include interactions and even iterative interactions with the clinician (step 160). The operation of a process step 200 implementing this step will be described more fully below.

Having calculated appliance definitions, the process 100 can proceed to the manufacturing step (step 180) in which appliances defined by the process are manufactured, or electronic or printed information is produced that can be used by a manual or automated process to define appliance configurations or changes to appliance configurations.

Figure 2:
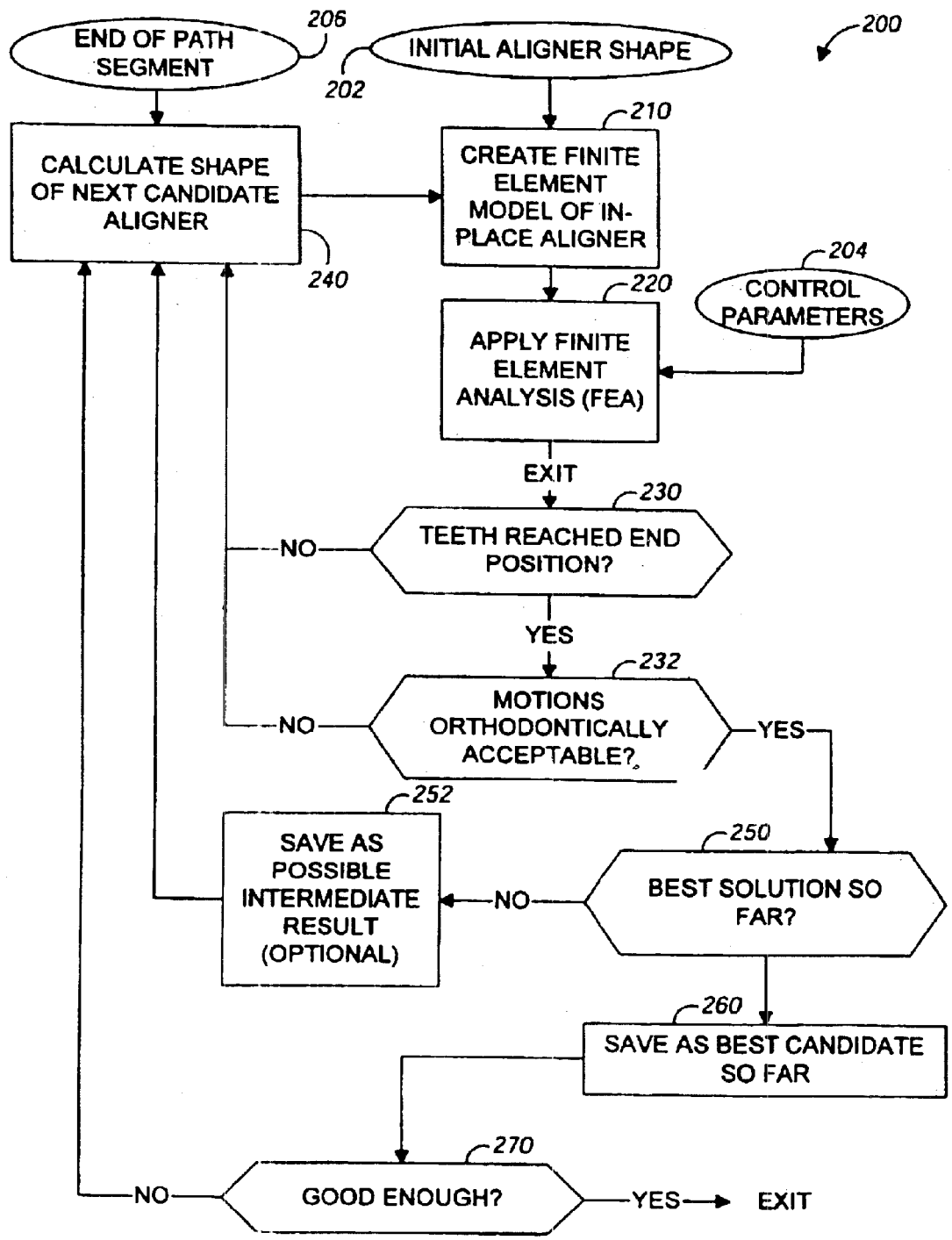
FIG. 2 is a flowchart of a process for calculating aligner shapes.

FIG. 2 illustrates a process 200 implementing the appliance-calculation step (FIG. 1, step 170) for polymeric shell aligners of the kind described in above-mentioned patent application Ser. No. 09/169,276. Inputs to the process include an initial aligner shape 202, various control parameters 204, and a desired end configuration for the teeth at the end of the current treatment path segment 206. Other inputs include digital models of the teeth in position in the jaw, models of the jaw tissue, and specifications of an initial aligner shape and of the aligner material. Using the input data, the process creates a finite element model of the aligner, teeth and tissue, with the aligner in place on the teeth (step 210). Next, the process applies a finite element analysis to the composite finite element model of aligner, teeth and tissue (step 220). The analysis runs until an exit condition is reached, at which time the process evaluates whether the teeth have reached the desired end position for the current path segment, or a position sufficiently close to the desired end position (step 230). If an acceptable end position is not reached by the teeth, the process calculates a new candidate aligner shape (step 240). If an acceptable end position is reached, the motions of the teeth calculated by the finite elements analysis are evaluated to determine whether they are orthodontically acceptable (step 232). If they are not, the process also proceeds to calculate a new candidate aligner shape (step 240). If the motions are orthodontically acceptable and the teeth have reached an acceptable position, the current aligner shape is compared to the previously calculated aligner shapes. If the current shape is the best solution so far (decision step 250), it is saved as the best candidate so far (step 260). If not, it is saved in an optional step as a possible intermediate result (step 252). If the current aligner shape is the best candidate so far, the process determines whether it is good enough to be accepted (decision step 270). If it is, the process exits. Otherwise, the process continues and calculates another candidate shape (step 240) for analysis.

The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, Calif. For creating finite element models and analyzing them, program products from a number of vendors can be used, including the PolyFEM product available from CADSI of Coralville, Iowa, the Pro/Mechanica simulation software available from Parametric Technology Corporation of Waltham, Massachusetts, the I-DEAS design software products available from Structural Dynamics Research Corporation (SDRC) of Cincinnati, Ohio, and the MSC/NASTRAN product available from MacNeal-Schwendler Corporation of Los Angeles, Calif.

Figure 3:
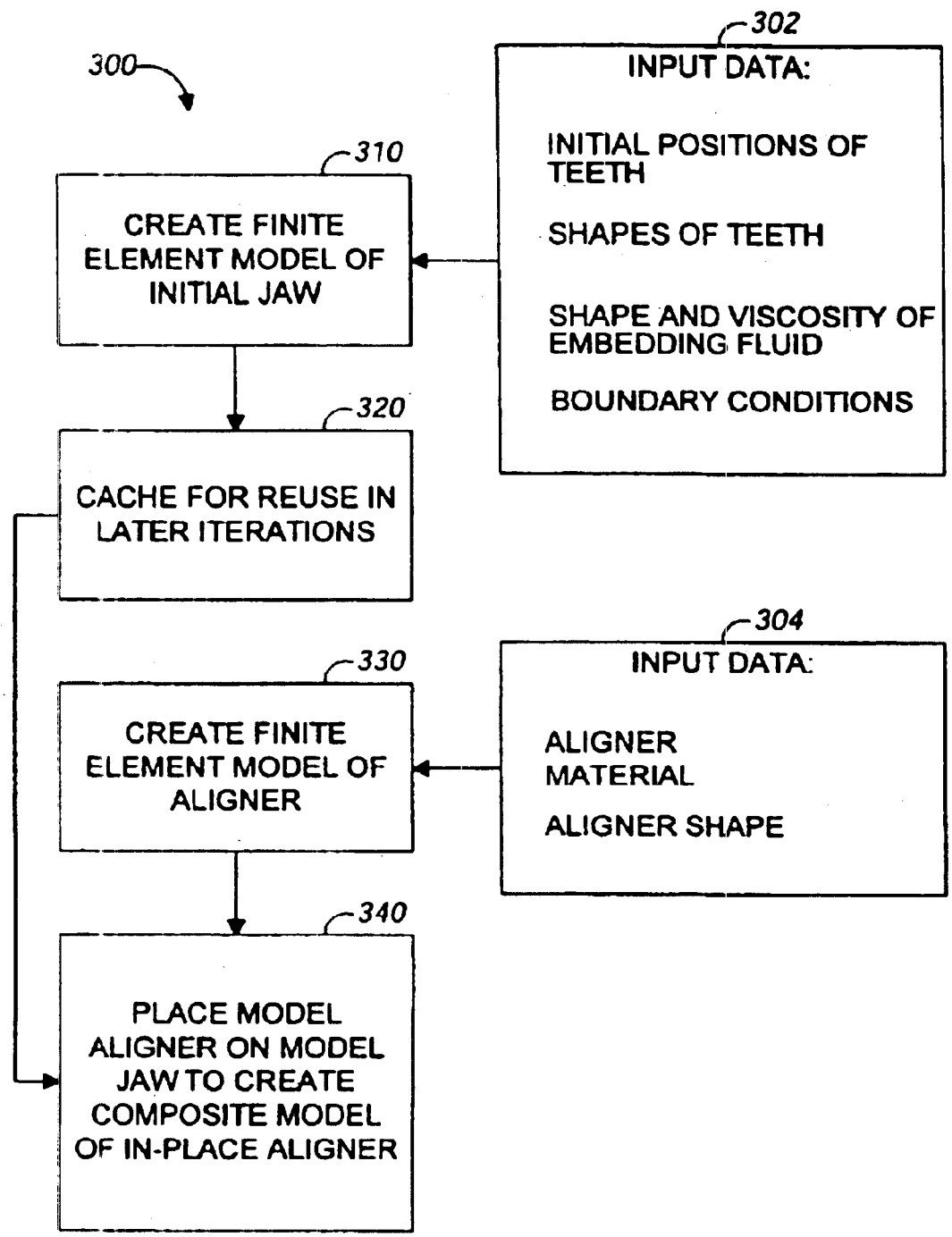
FIG. 3 is a flowchart of a subprocess for creating finite element models.

FIG. 3 shows a process 300 of creating a finite element model that can be used to perform step 210 of the process 200 (FIG. 2). Input to the model creation process 300 includes input data 302 describing the teeth and tissues and input data 304 describing the aligner. The input data describing the teeth 302 include the digital models of the teeth; digital models of rigid tissue structures, if available; shape and viscosity specifications for a highly viscous fluid modeling the substrate tissue in which the teeth are embedded and to which the teeth are connected, in the absence of specific models of those tissues; and boundary conditions specifying the immovable boundaries of the model elements. In one implementation, the model elements include only models of the teeth, a model of a highly viscous embedding substrate fluid, and boundary conditions that define, in effect, a rigid container in which the modeled fluid is held.

A finite element model of the initial configuration of the teeth and tissue is created (step 310) and optionally cached for reuse in later iterations of the process (step 320). As was done with the teeth and tissue, a finite element model is created of the polymeric shell aligner (step 330). The input data for this model includes data specifying the material of which the aligner is made and the shape of the aligner (data input 304).

The model aligner is then computationally manipulated to place it over the modeled teeth in the model jaw to create a composite model of an in-place aligner (step 340). Optionally, the forces required to deform the aligner to fit over the teeth, including any hardware attached to the teeth, are computed and used as a figure of merit in measuring the acceptability of the particular aligner configuration. In a simpler alternative, however, the aligner deformation is modeled by applying enough force to its insides to make it large enough to fit over the teeth, placing the model aligner over the model teeth in the composite model, setting the conditions of the model teeth and tissue to be infinitely rigid, and allowing the model aligner to relax into position over the fixed teeth. The surfaces of the aligner and the teeth are modeled to interact without friction at this stage, so that the aligner model achieves the correct initial configuration over the model teeth before finite element analysis is begun to find a solution to the composite model and compute the movement of the teeth under the influence of the distorted aligner.

Figure 4:
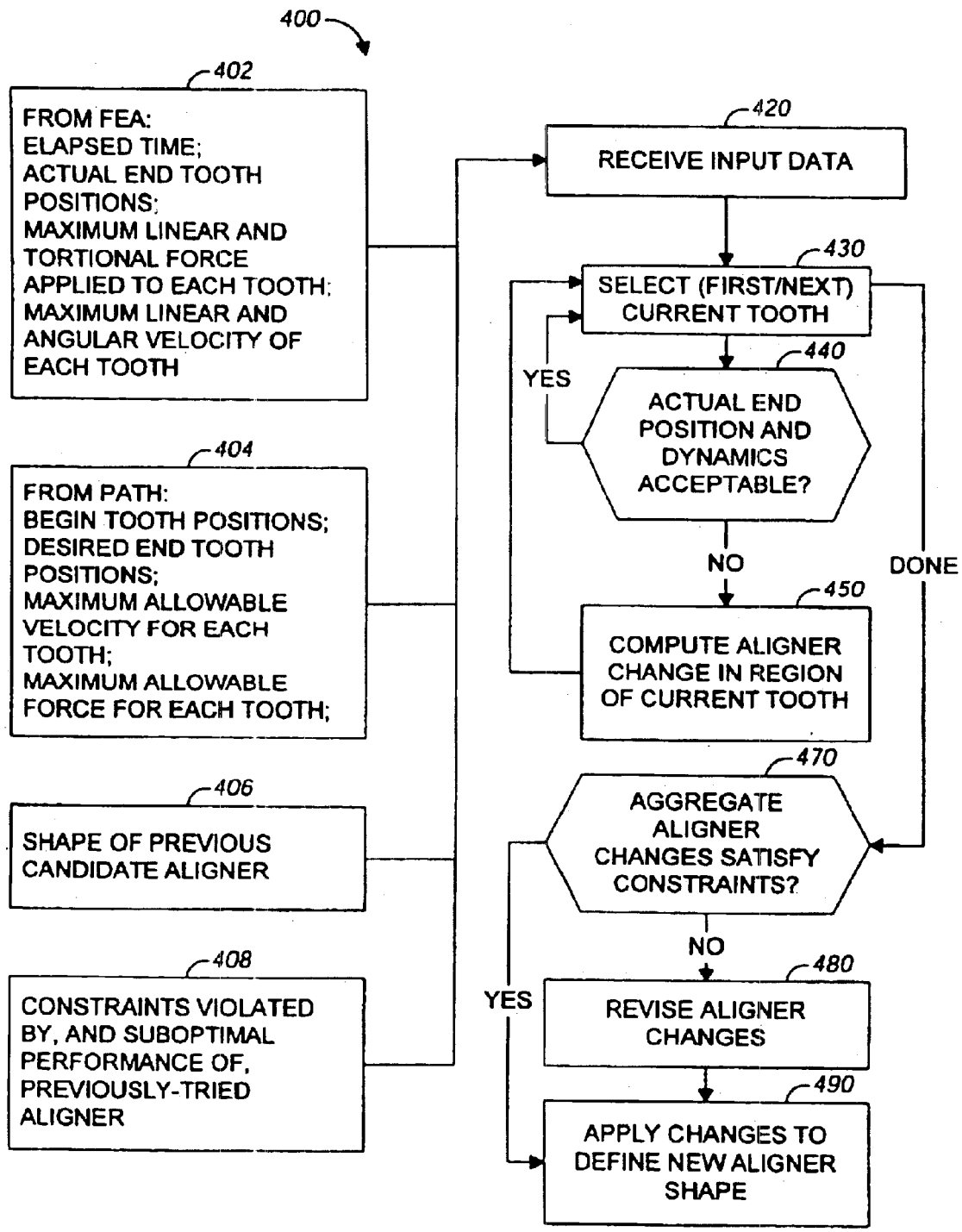
FIG. 4 is a flowchart of a subprocess for computing aligner changes.

FIG. 4 shows a process 400 for calculating the shape of a next aligner that can be used in the aligner calculations, step 240 of process 200 (FIG. 2). A variety of inputs are used to calculate the next candidate aligner shape. These include inputs 402 of data generated by the finite element analysis solution of the composite model and data 404 defined by the current tooth path. The data 402 derived from the finite element analysis includes the amount of real elapsed time over which the simulated repositioning of the teeth took place; the actual end tooth positions calculated by the analysis; the maximum linear and torsional force applied to each tooth; the maximum linear and angular velocity of each tooth. From the input path information, the input data 404 includes the initial tooth positions for the current path segment, the desired tooth positions at the end of the current path segment, the maximum allowable displacement velocity for each tooth, and the maximum allowable force of each kind for each tooth.

If a previously evaluated aligner was found to violate one or more constraints, additional input data 406 can optionally be used by the process 400. This data 406 can include information identifying the constraints violated by, and any identified suboptimal performance of, the previously evaluated aligner.

Having received the initial input data (step 420), the process iterates over the movable teeth in the model. (Some of the teeth may be identified as, and constrained to be, immobile.) If the end position and dynamics of motion of the currently selected tooth by the previously selected aligner is acceptable ("yes" branch of decision step 440), the process continues by selecting for consideration a next tooth (step 430) until all teeth have been considered ("done" branch from step 430 to step 470). Otherwise ("no" branch from step 440), a change in the aligner is calculated in the region of the currently selected tooth (step 450). The process then moves back to select the next current tooth (step 430) as has been described.

When all of the teeth have been considered, the aggregate changes made to the aligner are evaluated against previously defined constraints (step 470), examples of which have already been mentioned. Constraints can be defined with reference to a variety of further considerations, such as manufacturability. For example, constraints can be defined to set a maximum or minimum thickness of the aligner material, or to set a maximum or minimum coverage of the aligner over the crowns of the teeth. If the aligner constraints are satisfied, the changes are applied to define a new aligner shape (step 490). Otherwise, the changes to the aligner are revised to satisfy the constraints (step 480), and the revised changes are applied to define the new aligner shape (step 490).

Figure 5A:
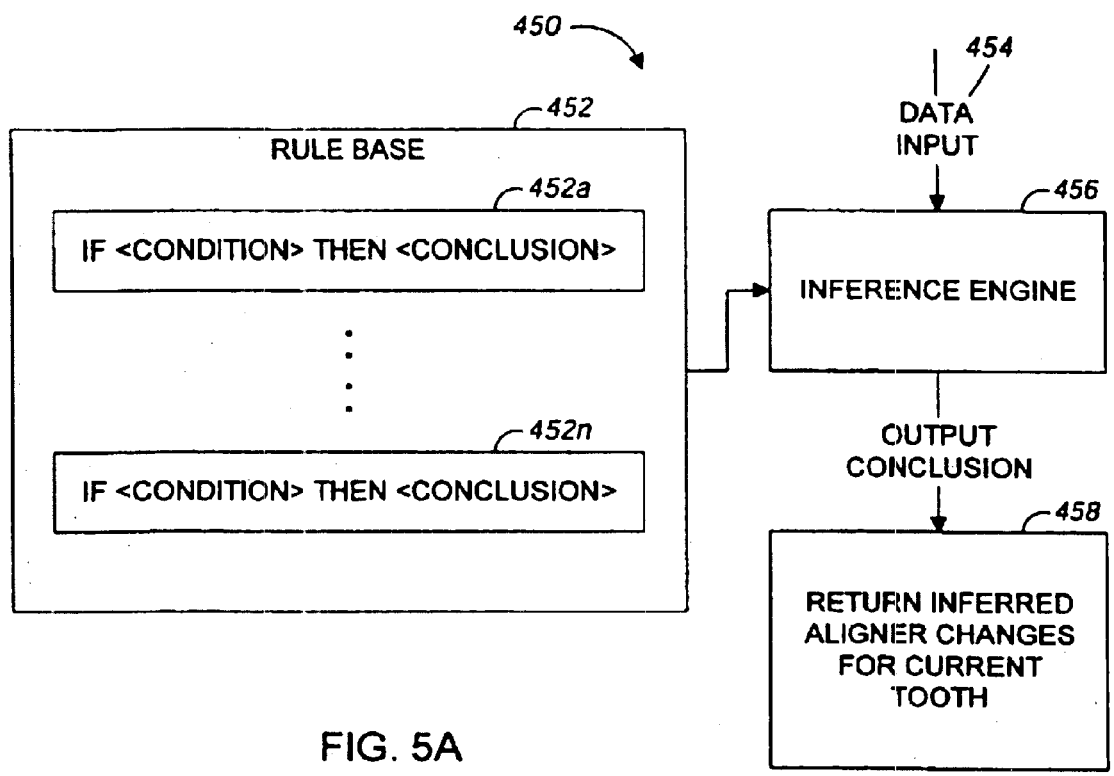
FIG. 5A is a flowchart of a subprocess for calculating changes in aligner shape.

FIG. 5A illustrates one implementation of the step of computing an aligner change in a region of a current tooth (step 450). In this implementation, a rule-based inference engine 456 is used to process the input data previously described (input 454) and a set of rules 452a–452n in a rule base of rules 452. The inference engine 456 and the rules 452 define a production system which, when applied to the factual input data, produces a set of output conclusions that specify the changes to be made to the aligner in the region of the current tooth (output 458).

Rules 452 have the conventional two-part form: an if-part defining a condition and a then-part defining a conclusion or action that is asserted if the condition is satisfied. Conditions can be simple or they can be complex conjunctions or disjunctions of multiple assertions. An exemplary set of rules, which defines changes to be made to the aligner, includes the following: if the motion of the tooth is too slow, add driving material to the aligner opposite the desired direction of motion; if the motion of the tooth is too slow, add driving material to overcorrect the position of the tooth; if the tooth is too far short of the desired end position, add material to overcorrect; if the tooth has been moved too far past the desired end position, add material to stiffen the aligner where the tooth moves to meet it; if a maximum amount of driving material has been added, add material to overcorrect the repositioning of the tooth and do not add driving material; if the motion of the tooth is in a direction other than the desired direction, remove and add material so as to redirect the tooth.

Figure 5B:
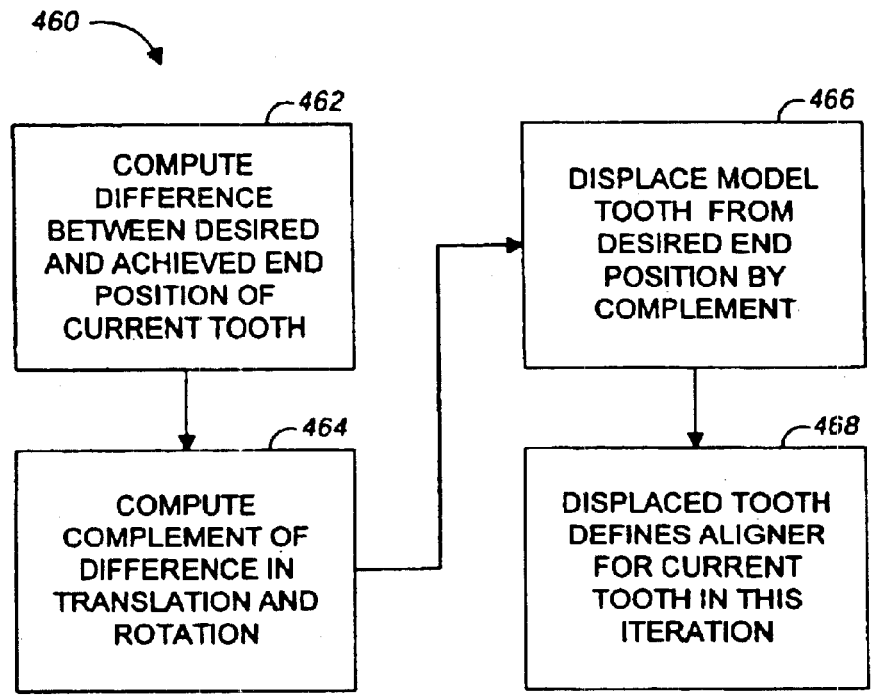
FIG. 5B is a flowchart of a subprocess for calculating changes in aligner shape.
Figure 5C:
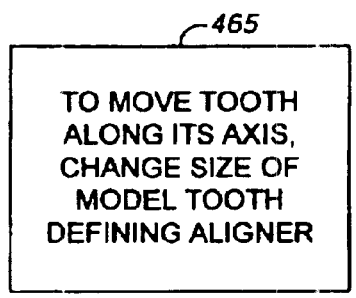
FIG. 5C is a flowchart of a subprocess for calculating changes in aligner shape.

In an alternative embodiment, illustrated in FIGS. 5B and 5C, an absolute configuration of the aligner is computed, rather than an incremental difference. As shown in FIG. 5B, a process 460 computes an absolute configuration for an aligner in a region of a current tooth. Using input data that has already been described, the process computes the difference between the desired end position and the achieved end position of the current tooth (462). Using the intersection of the tooth center line with the level of the gum tissue as the point of reference, the process computes the complement of the difference in all six degrees of freedom of motion, namely three degrees of translation and three degrees of rotation (step 464). Next, the model tooth is displaced from its desired end position by the amounts of the complement differences (step 466), which is illustrated in FIG. 5D.

Figure 5D:
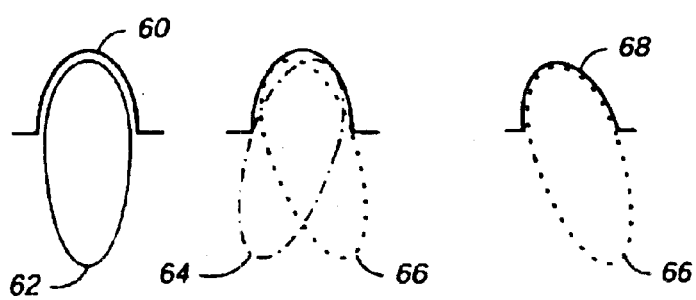
FIG. 5D is a schematic illustrating the operation of the subprocess of FIG. 5B.

FIG. 5D shows a planar view of an illustrative model aligner 60 over an illustrative model tooth 62. The tooth is in its desired end position and the aligner shape is defined by the tooth in this end position. The actual motion of the tooth calculated by the finite element analysis is illustrated as placing the tooth in position 64 rather than in the desired position 62. A complement of the computed end position is illustrated as position 66. The next step of process 460 (FIG. 5B) defines the aligner in the region of the current tooth in this iteration of the process by the position of the displaced model tooth (step 468) calculated in the preceding step (466). This computed aligner configuration in the region of the current tooth is illustrated in FIG. 5D as shape 68 which is defined by the repositioned model tooth in position 66.

A further step in process 460, which can also be implemented as a rule 452 (FIG. 5A), is shown in FIG. 5C. To move the current tooth in the direction of its central axis, the size of the model tooth defining that region of the aligner, or the amount of room allowed in the aligner for the tooth, is made smaller in the area away from which the process has decided to move the tooth (step 465).

Figure 6:
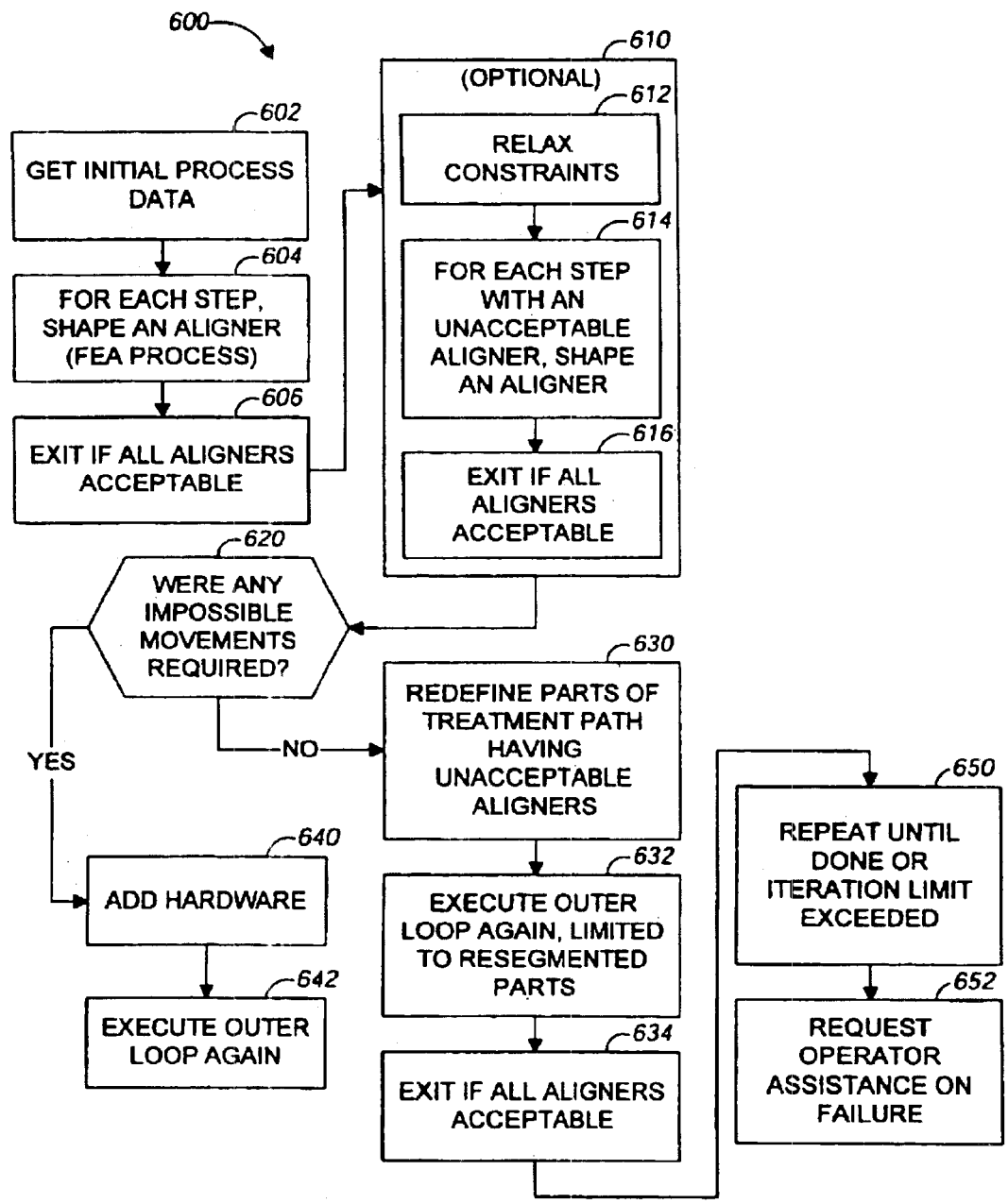
FIG. 6 is a flowchart of a process for computing shapes for sets of aligners.

As shown in FIG. 6, the process 200 of computing the shape for an aligner for a step in a treatment path is one step in an overall process 600 of computing the shapes of a series of aligners. This overall process 600 begins with an initialization step 602 in which initial data, control and constraint values are obtained.

When an aligner configuration has been found for each step or segment of the treatment path (step 604), the overall process 600 determines whether all of the aligners are acceptable (step 606). If they are, the process exits and is complete. Otherwise, the process optionally undertakes a set of steps 610 in an attempt to calculate a set of acceptable aligners. First, one or more of the constraints on the aligners is relaxed (step 612). Then, for each path segment with an unacceptable aligner, the process 200 of shaping an aligner is performed with the new constraints (step 614). If all the aligners are now acceptable, the overall process 600 exits (step 616).

Aligners may be unacceptable for a variety of reasons, some of which are handled by the overall process. For example, if any impossible movements were required (decision step 620), that is, if the shape calculation process 200 was required to effect a motion for which no rule or adjustment was available, the process 600 proceeds to execute a module that calculates the configuration of a hardware attachment to the subject tooth to which forces can be applied to effect the required motion (step 640). Because adding hardware can have an effect that is more than local, when hardware is added to the model, the outer loop of the overall process 600 is executed again (step 642).

If no impossible movements were required ("no" branch from step 620), the process transfers control to a path definition process (such as step 150, FIG. 1) to redefine those parts of the treatment path having unacceptable aligners (step 630). This step can include both changing the increments of tooth motion, i.e., changing the segmentation, on the treatment path, changing the path followed by one or more teeth in the treatment path, or both. After the treatment path has been redefined, the outer loop of the overall process is executed again (step 632). The recalculation is advantageously limited to recalculating only those aligners on the redefined portions of the treatment path. If all the aligners are now acceptable, the overall process exits (step 634). If unacceptable aligners still remain, the overall process can be repeated until an acceptable set of aligners is found or an iteration limit is exceeded (step 650). At this point, as well as at other point in the processes that are described in this specification, such as at the computation of additional hardware (step 640), the process can interact with a human operator, such as a clinician or technician, to request assistance (step 652). Assistance that an operator provides can include defining or selecting suitable attachments to be attached to a tooth or a bone, defining an added elastic element to provide a needed force for one or more segments of the treatment path, suggesting an alteration to the treatment path, either in the motion path of a tooth or in the segmentation of the treatment path, and approving a deviation from or relaxation of an operative constraint.

As was mentioned above, the overall process 600 is defined and parameterized by various items of input data (step 602). In one implementation, this initializing and defining data includes the following items: an iteration limit for the outer loop of the overall process; specification of figures of merit that are calculated to determine whether an aligner is good enough (see FIG. 2, step 270); a specification of the aligner material; a specification of the constraints that the shape or configuration of an aligner must satisfy to be acceptable; a specification of the forces and positioning motions and velocities that are orthodontically acceptable; an initial treatment path, which includes the motion path for each tooth and a segmentation of the treatment path into segments, each segment to be accomplished by one aligner, a specification of the shapes and positions of any anchors installed on the teeth or otherwise; and a specification of a model for the jaw bone and other tissues in or on which the teeth are situated (in the implementation being described, this model consists of a model of a viscous substrate fluid in which the teeth are embedded and which has boundary conditions that essentially define a container for the fluid).

Optionally, other features are added to the tooth model data sets to produce desired features in the aligners. For example, it may be desirable to add digital wax patches to define cavities or recesses to maintain a space between the aligner and particular regions of the teeth or jaw. It may also be desirable to add digital wax patches to define corrugated or other structural forms to create regions having particular stiffness or other structural properties. In manufacturing processes that rely on generation of positive models to produce the repositioning appliance, adding a wax patch to the digital model will generate a positive mold that has the same added wax patch geometry. This can be done globally in defining the base shape of the aligners or in the calculation of particular aligner shapes. One feature that can be added is a rim around the gumline, which can be produced by adding a digital model wire at the gumline of the digital model teeth from which the aligner is manufactured. When an aligner is manufactured by pressure fitting polymeric material over a positive physical model of the digital teeth, the wire along the gumlines causes the aligner to have a rim around it providing additional stiffness along the gumline.

In another optional manufacturing technique, two sheets of material are pressure fit over the positive tooth model, where one of the sheets is cut along the apex arch of the aligner and the other is overlaid on top. This provides a double thickness of aligner material along the vertical walls of the teeth.

The changes that can be made to the design of an aligner are constrained by the manufacturing technique that will be used to produce it. For example, if the aligner will be made by pressure fitting a polymeric sheet over a positive model, the thickness of the aligner is determined by the thickness of the sheet. As a consequence, the system will generally adjust the performance of the aligner by changing the orientation of the model teeth, the sizes of parts of the model teeth, the position and selection of attachments, and the addition or removal of material (e.g., adding wires or creating dimples) to change the structure of the aligner. The system can optionally adjust the aligner by specifying that one or more of the aligners are to be made of a sheet of a thickness other than the standard one, to provide more or less force to the teeth. On the other hand, if the aligner will be made by a stereo lithography process, the thickness of the aligner can be varied locally, and structural features such as rims, dimples, and corrugations can be added without modifying the digital model of the teeth.

The system can also be used to model the effects of more traditional appliances such as retainers and braces and therefore be used to generate optimal designs and treatment programs for particular patients.

The data processing aspects of the invention can be implemented in digital electronic circuitry, or in computer hardware, firmware, software, or in combinations of them. Data processing apparatus of the invention can be implemented in a computer program product tangibly embodied in a machine-readable storage device for execution by a programmable processor; and data processing method steps of the invention can be performed by a programmable processor executing a program of instructions to perform functions of the invention by operating on input data and generating output. The data processing aspects of the invention can be implemented advantageously in one or more computer programs that are executable on a programmable system including at least one programmable processor coupled to receive data and instructions from and to transmit data and instructions to a data storage system, at least one input device, and at least one output device. Each computer program can be implemented in a high-level procedural or object oriented programming language, or in assembly or machine language, if desired; and, in any case, the language can be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

To provide for interaction with a user, the invention can be implemented using a computer system having a display device such as a monitor or LCD (liquid crystal display) screen for displaying information to the user and input devices by which the user can provide input to the computer system such as a keyboard, a two-dimensional pointing device such as a mouse or a trackball, or a three-dimensional pointing device such as a data glove or a gyroscopic mouse. The computer system can be programmed to provide a graphical user interface through which computer programs interact with users. The computer system can be programmed to provide a virtual reality, three-dimensional display interface.

The invention has been described in terms of particular embodiments. Other embodiments are within the scope of the following claims. For example, the steps of the invention can be performed in a different order and still achieve desirable results.

What is claimed is:

1. A computer-implemented method for segmenting an orthodontic treatment path into clinically appropriate substeps for repositioning the teeth of a patient, comprising:

providing a digital model of the shape and material of each of a sequence of appliances to be applied to a scanned model of the teeth;

computing the actual effect of the appliances on the teeth by performing finite element analysis on each of said models;

evaluating the effect against clinical constraints; and generating data sets corresponding to a plurality of appliances having geometries selected to progressively reposition the teeth, wherein the appliances comprise polymeric shells having cavities and wherein the cavities of successive shells have different geometries shaped to receive and resiliently reposition teeth from one arrangement to a successive arrangement.

2. A method as in claim 1, further comprising fabricating individual polymeric shell appliances based on individual ones of the data sets.

3. The method of claim 2, wherein the appliances are manufactured by fitting polymeric sheets over positive models corresponding to the data sets.

4. The method of claim 1, wherein the sequence of appliances includes a sequence of polymeric shells manufactured by stereo lithography from digital models.

5. The method of claim 1, further comprising:

comparing the actual effect of the appliances with an intended effect of the appliances;

identifying an appliance as an unsatisfactory appliance if the actual effect of the appliance is more than a threshold different from the intended effect of the appliance; and modifying a model of the unsatisfactory appliance according to the results of the comparison.

6. The method of claim 5, wherein the model of the unsatisfactory appliance is modified by modifying the shape of the unsatisfactory appliance.

7. The method of claim 6, wherein the shape of the unsatisfactory appliance is modified by adding a dimple.

8. The method of claim 6, wherein the shape of the unsatisfactory appliance is modified by adding material to cause an overcorrection of tooth position.

9. The method of claim 6, wherein the shape of the unsatisfactory appliance is modified by adding a ridge of material to increase stiffness.

10. The method of claim 6, wherein the shape of the unsatisfactory appliance is modified by adding a rim of material along a gumline to increase stiffness.

11. The method of claim 6, wherein the shape of the unsatisfactory appliance is modified by removing material to reduce stiffness.

12. The method of claim 5, wherein the unsatisfactory appliance is redefined to have a shape defined by the complement of the difference between the intended effect and the actual effect of the unsatisfactory appliance.

13. The method of claim 1, wherein the clinical constraints include a maximum rate of displacement of a tooth, a maximum force on a tooth, and a desired end position of a tooth.

14. The method of claim 13, wherein the maximum force is a linear force or a torsional force.

15. The method of claim 13, wherein the maximum rate of displacement is a linear or a angular rate of displacement.

* * * * *